United States Patent [19]

Fakoukakis et al.

[11] Patent Number: 4,956,478
[45] Date of Patent: Sep. 11, 1990

[54] METHOD FOR THE PRODUCTION OF ALKENYL-SUCCINIC ANHYDRIDES

[75] Inventors: Emanuel P. Fakoukakis, Brussels; Sorin V. Mustatea, Loncin, both of Belgium; Günter Bellmann, Commugny, Switzerland

[73] Assignee: The Procter & Gamble Company, Cincinnati, Ohio

[21] Appl. No.: 406,938

[22] Filed: Sep. 13, 1989

[30] Foreign Application Priority Data

Sep. 14, 1988 [EP]  European Pat. Off. ........ 88810624.2

[51] Int. Cl.$^5$ ........................................... C07D 307/60
[52] U.S. Cl. ................................................... 549/255
[58] Field of Search ......................................... 549/255

[56] References Cited

U.S. PATENT DOCUMENTS 2,411,215  1/1943  Kise et al. ............................ 549/255
3,412,111  11/1968  Irwin et al. ......................... 549/255

*Primary Examiner*—John M. Ford
*Assistant Examiner*—Bernard I. Dentz
*Attorney, Agent, or Firm*—Donald E. Hasse; Thomas H. O'Flaherty; Richard C. Witte

[57] ABSTRACT

This method which involves reacting maleic anhydride and α-olefins in an autoclave at about 200°–250° C. gives particularly good results and produces alkenyl-succinic anhydrides which need not be purified by distillation when using, as the starting α-olefins, dodecene containing a substantial amount of tetradecene.

8 Claims, No Drawings

METHOD FOR THE PRODUCTION OF ALKENYL-SUCCINIC ANHYDRIDES

The present invention relates to the preparation of alkenyl-succinic anhydride compounds by the reaction of α-monoolefins with maleic anhydride (MA).

Alkenyl-succinic anhydrides are useful industrial compounds. Quoted fields of use are curing agents for synthetic resins, elastomer components, rust and corrosion inhibitors, additives for increasing viscosity in paints and greases, foam suppression, pesticides and fungicides, surfactant additives, plasticizers, intermediates in synthetic chemistry and drug manufacture, etc..

The chemistry of the reaction between MA and α-olefins resulting from the extraction or cracking of natural oils has been well investigated and described in literature and patents.

For instance U.S. Pat. Nos. 2,411,215 (KISE et al) and 3,412,111 (IRWIN et al) provide a detailed list of useful operating parameters and conditions pertaining to this reaction. The molar ratio of olefin ($C_3$ to $C_{60}$-olefins) to MA can be comprised between about 0.5 to 20 and the reaction can be carried out at temperatures of about 160° C. to about 300° C. for 0.1 to 48 hrs under pressures of about 1 to 1000 lb/square inch (0.069 bar to 69 bar). U.S. Pat. No. 2,411,215 specifies that yields in this reaction are improved if the reaction medium is well homogeneous, i.e. if the MA is completely dissolved in the α-olefins prior to reaction; this can be effected by stirring the ingredients together beforehand at temperatures below 200° C., the reaction proper being carried out afterwards at temperatures above 200° C.

Another technique to increase the yields and to reduce the proportion of undesirable polymeric side-products (gums) which sometimes contaminate the desired alkylene-succinic anhydrides is to add polymerization inhibitors to the reaction mixture. This technique is particularly emphasized in U.S. Pat. No. 3,412,111. In this case the preferred inhibitors are aromatic sulfur or hydroxy compounds, e.g. 2,2-bis(p-hydroxyphenyl)-propane, hydroquinone and phenothiazine.

At the end of the reaction period, the reaction mixture can be treated in any suitable manner to recover the individual components therein, e.g. by distillation. U.S. Pat. No. 2,411,215 teaches to first drain the gums which accumulate to the bottom of the reaction vessel, then transfer the liquid phase in a flash evaporator in which unreacted MA and α-olefins will evaporate and be recovered by condensation. The residue from the flash evaporator is then distilled in a still for purifying the desired alkenyl-succinic anhydride compounds from remaining residual by-products.

In U.S. Pat. No. 3,412,111, there is recommended to effect distillation of the crude reaction product at temperatures of about 50° C. to about 250° C. under about $10^{-4}$ to about 15 lb/square inch ($5 \times 10^{-3}$–760 Torr) to recover unreacted olefin and maleic anhydride (if any present) and purify the desired alkenyl succinic anhydrides.

Although the processes reported in the literature have much merit, it was desirable to still bring improvements thereto, e.g. render the reaction operation simpler, more efficient and more economical, and providing products ready to be used in many instances without further purification by distillation. It was inter alia desirable to decrease as much as possible the production of polymeric side products of the kind disclosed in the prior art. In this connection, it is noted that, even under the optimal disclosed conditions (see U.S. Pat. No. 3,412,111) the amount of polymers which had to be separated from the desired product was still 12 g in the case of using a mixture of 2 moles of dodecene (337 g) and one mole of MA (98 g) and operating in the presence of phenothiazine. Furthermore, using phenothiazine as an inhibitor was shown to be undesirable by the present inventors as it usually provides a dark colored product.

It was however found quite unexpectedly by the present inventors that using, as the starting α-olefins, a 1:1 to 4:1 by weight mixture, preferably 65:35, of dodecene (D) and tetradecene (T) ($C_{12}$ and $C_{14}$ α-olefins), substantially no polymeric residue was any longer contaminating the desired alkenyl-succinic anhydrides and, as a consequence, the latter can be used in many instances without further purification by distillation. Thus, the method of the present invention which results from this surprising discovery is defined in annexed claim 1.

The reasons why this progress arose has not been elucidated. It is however supposed that a factor is the efficient solubility of maleic anhydride in the aforementioned DT mixture, particularly 65:35 by weight, at temperatures below 200° C., this effect leading to the formation of substantially well homogeneous solutions of the reactants before reaction.

Another factor of improvement is the efficient control of the reaction time in view of the fact that undesirable side products probably form at the end of the reaction between small quantities of unreacted MA and the desired alkenyl-succinic anhydrides. It may therefore be advantageous to stop the reaction at a time before it goes to full completion relative to the MA used, e.g. when only 80 to 95% of the MA has been consumed, and then proceed with the recovery of unreacted materials by reduced pressure distillation. The somewhat reduced yield of alkenyl-succinic anhydride experienced then is entirely compensated by the clean recovery of the unused MA and α-olefins which can be, of course, recycled. It is noted in this connection, that in the case of operating with batches of about 1 to 5 kg of starting materials reacted at 220°–240° C., the preferred reaction times are in the order of 1–10 hrs, more preferably 2–3 hrs.

The polymerization inhibitors to be used in this reaction can be those reported in U.S. Pat. No. 3,412,111 incorporated herein by reference. Phenothiazine for instance is effective but, as said before, provides colored products; consequently non-sulfur inhibitors like hydroquinone are preferred. Excellent results are recorded with mono-etherified hydroquinone, e.g. hydroquinone-lower alkoxy-monoethers such as the monomethyl- or -ethyl hydroquinones.

In general the following batch procedure can be carried out to embody the method of the invention:

The 1:1 to 4:1, by weight mixture of D and T, preferably 65:35 by weight (1–5 molar equivalents, preferably 1–2 equiv.) is placed in an autoclave with 0.1 to 2% by weight of inhibitor (calculated on the MA) and heated progressively under a blanket of inert gas (e.g. $N_2$, $CO_2$ or argon) to a temperature of about 160°–200° C., preferably 170°–180° C., and the MA (1 molar equivalent) is added in liquid (molten) form under stirring. At these temperatures, as said before, the solubility of the MA in the α-olefins mixture is satisfactory; separate experiments in the present work have shown that it is about 20–25% by weight at 160°–180° C. When the dissolution is complete and the solution is homogeneous, the vessel is sealingly closed and the temperature is raised to a value above 200° C., preferably 220°–250° C., for a period of time of 1–10 hrs, preferably 2–3 hrs, depending on the desired degree of reaction completion. During the reaction a pressure rise is experienced of about 2–2.5 bar (not exceeding 4–5 bar). With the longer reaction times, e.g. 5–10 hrs, the MA is substantially fully consumed and the amount of it which can be recovered after the end of the reaction is small or negligible. With the shorter reaction times, the amount of unreacted MA is greater but it can be recovered cleanly for recycling at the end of the reaction and the reaction products have a lighter color.

Then, when the reaction is over, heating is discontinued and the reaction mixture is subjected to distillation to recover the unreacted starting materials. During this distillation, it is important that the condenser be kept at the right temperature to avoid plugging by solidified maleic anhydride which solidifies at about 60° C. An appropriate condenser temperature is about 61°–70° C. and the pressure during distillation is preferably 12–20 Torr, at least at start.

After distillation, the residue is collected and consists of a mixture of dodecenyl- and tetradecenyl-succinic anhydride in proportions substantially equivalent to that in the starting mixture of α-olefins. This reaction product is pure enough for most applications and can be used as such without further purification. The collected recovered α-olefins (the relative proportion of which remains substantially constant) and the MA can then be recycled in a next run without problems since their purity is about equivalent to that of the starting materials.

Although the foregoing general conditions have been described with reference to a batch process, it is obvious that they also apply to a continuous process. In this case, the key components comprise a preliminary mixing chamber into which the α-olefin mixture containing the inhibitor and the molten maleic anhydride are fed simultaneously in a correct mole ratio and of sufficient volume retention time to ensure complete dissolution of the MA in the α-olefins; this preliminary chamber is followed by a line-reactor (e.g. a chamber or a coil) of sufficient length to ensure proper heating of the reactants for the desired time. After reaction, the mixture can be subjected to continuous distillation by usual procedures and using conventional equipment to assure continuous separation of the products and recycling of unused reactants.

The following Examples illustrate the invention in more detail.

EXAMPLES 1 to 9

A 65:35 (by weight) mixture of $C_{12}$–$C_{14}$ α-olefins containing 1708 g (10.15 moles) of dodecene (D) and 919 g (4.68 moles) of tetradecene (T) and 7.3 g of hydroquinone was heated to 170° C. under nitrogen in a 5-liter autoclave. 726 g (7.40 moles) of molten (100° C.) maleic anhydride (MA) were added under stirring and the vessel was tightly closed. After the solution had become homogeneous (192° C.), the temperature was raised to 220° C. and maintained there for 3 hrs.

The reaction mixture was distilled in a "Rotavapor" (BUCHI, type EL-131) under reduced pressure starting under 14 Torr and ending under 1.6 Torr (bath temperature 150° C.). Under these conditions, the approximate boiling temperatures (14 Torr) of the components are: MA 80° C.; D 100° C.; T 125° C. The condenser was kept at 63° C. (thermostated water circulation) to prevent plugging of the apparatus by distilled MA. After distillation, the light colored residue 1940 g (yield 95%) was shown by analysis to be a nearly pure mixture of $C_{12}$-and $C_{14}$-alkenyl-succinic anhydrides (DTSA) in a molar ratio very close to that (10.2/4.7) of the initial olefins. The distillate (1389 g) separated into a liquid and a solid phase (17.6 g) which was shown later to be maleic anhydride. The liquid phase was the recovered α-olefins mixture, the components being in a ratio similar to that of the starting material. Taking into account that the solubility of MA in the hydrocarbon mixture at room temperature is about 0.3%, the yield of recovered MA is approximately 3%. The yield of recovered olefins which can be directly recycled in a subsequent run approximates the theoretical value.

Other Examples in which the various parameters involved were varied like temperature, reaction time, mole ratio of D+T to MA, nature of inhibitor (always 1% by weight relative to MA) were run similarly and the data are reported in the Table 1 below. In the Table the % recovered D+T mixture is calculated on the theoretically unused portion (excess of D+T) with the exception of Example 6 (stoichiometric amount of reactants) were the quoted figure is the actual value.

TABLE 1

| | Starting materials | | | | | Products | | |
|---|---|---|---|---|---|---|---|---|
| Example No. | D + T mixture (moles) | D + T/MA mole ratio | Inhibitor | Temp. (°C.) | Time (hrs) | DTSA (%) | D + T (%) | MA (%) |
| 1 | 14.8 | 2 | none | 220 | 8 | 96.4 | 101.5 | — |
| 2 | 14.8 | 2 | PT | 220 | 8 | 97.7 | 102.2 | — |
| 3 | 14.8 | 2 | HQ | 220 | 8 | 98.2 | 100.8 | — |
| 4 | 14.8 | 2 | HQME | 220 | 8 | 96.2 | 103.0 | — |
| 5 | 13.8 | 1.5 | HQ | 220 | 8 | 94.6 | 112.6 | — |
| 6 | 12.2 | 1 | HQ | 220 | 8 | 88.2 | 13.5 | 0.2 |
| 7 | 14.8 | 2 | HQ | 220 | 3 | 95.1 | 103.9 | 3.0 |
| 8 | 13.8 | 1.5 | HQ | 240 | 8 | 94.8 | 111.8 | — |
| 9 | 13.8 | 1.5 | HQ | 220 | 2 | 89.5 | 119.5 | 10.1 |

Codes:
PT = phenothiazine
HQ = hydroquinone
ME = monomethylether hydroquinone

EXAMPLE 10

(1:1 by weight D:T mixture)

A mixture of 1258.2 g (7.48 moles) of dodecene, 1258.2 g (6.41 moles) of tetradecene (total 13.88 moles), 902 g (9.19 moles) of maleic anhydride and 9 g of hydroquinone was stirred and heated to 190° C. in a pressure reactor as in the previous examples until homogeneous.

Then the temperature was raised to 220° C. under sealed conditions, whereby the reaction started. The temperature was maintained and samples were taken at intervals of time through a bottom outlet valve of the reactor and analyzed by usual means for concentration of constituents (see thereafter). The results are given in Table 2 in % by weight up to a period of 5 hrs.

TABLE 2

| Time (hrs) | MA | D | T | DTSA 12 | DTSA 14 |
|---|---|---|---|---|---|
| 0 | 26.3 | 36.7 | 36.7 | 0 | 0 |
| ½ | 11.6 | 18.8 | 18.4 | 14.9 | 15.7 |
| 1 | 7.14 | 17.1 | 17.9 | 19.2 | 20.2 |
| 2 | 3.21 | 14.4 | 14.1 | 21.0 | 21.8 |
| 3 | 1.38 | 13.5 | 13.7 | 22.5 | 23.1 |
| 4 | 0.60 | 13.6 | 13.6 | 24.2 | 24.6 |
| 5 | 0.28 | 14.9 | 14.0 | 25.5 | 25.9 |

After 5 hrs, the reaction was stopped and the mixture (3409 g) subjected to vacuum distillation (bath 150° C.) as indicated in the previous examples; a total of 896 g (4.94 moles) of unreacted D and T olefins of weight ratio substantially near 1:1 was collected, wereby the yield of DTSA based on used up olefins (i.e. 8.94 moles) and the residue weight (2496 g ≈8.9 moles) was about 99%.

EXAMPLE 11

(4:1 by weight D/T mixture)

The reaction conditions and subsequent manipulations were repeated exactly as in Example 10 using the following components and conditions:

| | |
|---|---|
| Dodecene | 2013.1 g (11.96 moles) |
| Tetradecene | 503.3 g (2.55 moles) |
| Maleic anhydride | 902.1 g (9.2 moles) |
| Hydroquinone | 9 g |
| D + T/MA ratio | (1.58 mole/mole) |
| Reaction time | 5 hrs |
| Reaction temperature | 220° C. |
| Distillation of reaction mixture | 150° C./15-4 Torr |

Analyses performed as in the previous example are reported in Table 3 below.

TABLE 3

| Time (hrs) | MA | D | T | DTSA 12 | DTSA 14 |
|---|---|---|---|---|---|
| 0 | 26.3 | 58.7 | 14.7 | 0 | 0 |
| ½ | 12.0 | 37.2 | 10.7 | 25.3 | 6.6 |
| 1 | 7.51 | 30.0 | 8.5 | 29.2 | 8.6 |
| 2 | 2.62 | 21.8 | 5.6 | 38.6 | 9.8 |
| 3 | 1.45 | 21.9 | 5.6 | 41.9 | 10.5 |
| 4 | 0.53 | 22.5 | 6.2 | 44.3 | 13.3 |
| 5 | 0.22 | 21.7 | 6.1 | 42.5 | 11.7 |

Distillation provided 9.83 g (5.6 moles) of olefins and 2421 g (8.9 moles) of DTSA. Hence the overall yield of DTSA was about 99%.

ANALYSES

The reaction mixture was analyzed by sampling through a bottom outlet valve of the reactor and subjecting to GLC.

The gas-liquid chromatograph was a "CARLO ERBA Fractovap Series 4160" equipped with a 30 m×0.32 mm J & W fused silica capillary column (liquid phase: 0.25 μm DB-5).

carrier gas: $H_2$, 1.5 ml/min, inlet pressure 0.4 atm.
detector: FID, range 10 mv, attenuation 8, temperature 250° C.
injection: 1-1.5 μl, split ~1/9, temperature 230° C.
column temperature: initial: 80° C. for 2 min, final: 240° C. for 7 min, heating rate 10° C./min.

We claim:

1. A method for manufacturing alkenyl-succinic anhydrides in a form sufficiently pure for using them directly, this method including the steps of:
   (a) mixing one molar equivalent of maleic anhydride (MA) with α-monoolefins in a quantity corresponding to at least one olefinic bond molar equivalent and heating to a temperature below 200° C. but sufficient to ensure complete dissolution of the MA in the monoolefins and forming a homogeneous solution;
   (b) heating this homogeneous solution in a closed vessel to a temperature between 200° and 260° C. where the reaction between the MA and the olefin proceeds smoothly to substantially near or full completion relative to the amount of MA used;
   (c) distilling off unreacted α-olefins and MA, if any, and isolating the alkenyl-succinic anhydride products for further end-uses,
   which comprises using as the starting α-monoolefins a 1:1 to 4:1 by weight mixture of dodecene and tetradecene, whereby no significant formation of polymeric by-products is observed, and isolating the desired alkenyl-succinic anhydride products by simply collecting the residue of distillation of step (c), no further purification being needed.

2. The method of claim 1, wherein dissolution in step (a) is performed at 160°-180° C. and step (b) is performed for 0.2 to 10 hrs at 220°-240° C.

3. The method of claim 2, wherein step (b) is carried out for 2-3 hrs and the amount of consumed MA is 80-95% by weight.

4. The method of claim 1, which comprises adding 0.1-2% of a polymerization inhibitor to the reaction solution.

5. The method of claim 4, wherein the inhibitor is selected from at least one of hydroquinone, monoethers of hydroquinone and phenothiazine.

6. The method of claim 1, which comprises recycling the unreacted α-olefins and/or MA recovered from step (c).

7. The method of claim 1, wherein the distillation in step (c) is effected under 12-20 Torr, the condenser temperature being controlled to a value above the melting temperature of MA.

8. The method of claim 1, wherein the starting mono-α-olefins mixture is a 65:35 by weight mixture of dodecene and tetradecene.

* * * * *